(12) United States Patent
Zhang

(10) Patent No.: US 11,620,892 B2
(45) Date of Patent: Apr. 4, 2023

(54) CO ALARM FOR BATTERY TYPE GENERATOR

(71) Applicant: Shaoxing Dushang Yicheng Electric Machinery Co., Ltd., Zhejiang (CN)

(72) Inventor: Wangfu Zhang, Zhejiang (CN)

(73) Assignee: Shaoxing Dushang Yicheng Electric Machinery Co., Ltd., Shaoxing (CN)

( * ) Notice: Subject to any disclaimer, the term of this patent is extended or adjusted under 35 U.S.C. 154(b) by 0 days.

(21) Appl. No.: 17/492,674

(22) Filed: Oct. 3, 2021

(65) Prior Publication Data

US 2022/0415151 A1 Dec. 29, 2022

(30) Foreign Application Priority Data

Jun. 23, 2021 (CN) .......................... 202110697034.0

(51) Int. Cl.
*G08B 17/117* (2006.01)
*G08B 29/14* (2006.01)
*G01N 33/00* (2006.01)
*H03F 3/45* (2006.01)

(52) U.S. Cl.
CPC .......... *G08B 17/117* (2013.01); *G01N 33/004* (2013.01); *G08B 29/145* (2013.01); *H03F 3/45475* (2013.01)

(58) Field of Classification Search
CPC ...... G08B 21/16; G08B 21/185; G08B 21/18; G08B 21/02; F02P 11/06
See application file for complete search history.

(56) References Cited

U.S. PATENT DOCUMENTS

| 2012/0017600 A1* | 1/2012 | Saito | F02C 3/10 60/773 |
| 2022/0085646 A1* | 3/2022 | Lei | H02J 1/122 |
| 2022/0268722 A1* | 8/2022 | Osswald | G01N 7/08 |

FOREIGN PATENT DOCUMENTS

CN 111028459 A * 4/2020 ............. G08B 17/00

* cited by examiner

*Primary Examiner* — Mirza F Alam

(57) ABSTRACT

The present invention discloses a CO alarm for a battery type generator, comprising a MCU control unit U2, configured to analyze and process signals, which is in a deep sleep state when the generator is not running, and enters a sleep plus timing wake-up working state after the engine is running; a CO sensor detection unit U3 connected to the MCU control unit, configured to convert the CO concentration in the environment into a corresponding electrical signal and output to the MCU control unit U2 for processing; an alarm indication unit U4 connected to the MCU control unit, configured to give an alarm prompt for the CO concentration and an alarm failure prompt.

6 Claims, 4 Drawing Sheets

CO ALARM FOR BATTERY TYPE GENERATOR

CROSS REFERENCE TO RELATED APPLICATIONS

The present application claims the benefit of Chinese Patent Application No. 202110697034.0 filed on Jun. 23, 2021, the contents of which are incorporated herein by reference in their entirety.

TECHNICAL FIELD

The present invention relates to the technical field of CO alarms, and in particular to a CO alarm for a battery type generator.

BACKGROUND

Portable generators are widely used because of their small size, mobility, and strong adaptability to the working environment, etc. However, because this type of generator drives a magneto to output power using a gasoline engine, a large amount of CO harmful gas will be generated during use. In many household applications, many accidents of casualties happen because of ignoring the CO emission problems. In many countries, to meet the safety requirements, mandatory installation of CO alarms has been implemented. In order to meet the market demands, the present invention provides a CO alarm for a battery type generator.

SUMMARY

In order to overcome the shortcomings of the prior art, the present invention provides a CO alarm for a battery type generator.

In order to achieve the above object, the present invention adopts the following technical solutions. A CO alarm for a battery type generator, comprising:

a MCU control unit U2, configured to analyze and process signals, which is in a deep sleep state when the generator is not running, and enters a sleep plus timing wake-up working state after the engine is running;

a CO sensor detection unit U3 connected to the MCU control unit, configured to convert the CO concentration in the environment into a corresponding electrical signal and output to the MCU control unit U2 for processing;

an alarm indication unit U4 connected to the MCU control unit, configured to give an alarm prompt for the CO concentration and an alarm failure prompt;

a speed detection unit U5 connected to the MCU control unit, configured to collect the running status of the generator and wake up the MCU control unit U2 from the deep sleep state to the normal working state;

a flameout control unit U6 connected to the MCU control unit, configured to shut down the generator when the alarm fails or the CO concentration alarms;

a battery power supply unit U1, configured to provide a working power supply required for the entire CO alarm; when the generator generates excessive CO, the CO concentration in the environment is converted into a corresponding electrical signal by the CO sensor detection unit U3 to output to the MCU control unit U2 for processing. After processing by the MCU control unit U2, the signal is sent to the alarm indication unit and the flameout control unit, to give an alarm prompt of the CO concentration and shut down the generator, thereby preventing safety accidents.

Preferably, the battery supply unit comprises a battery BT1 and a capacitor C1.

Preferably, the MCU control unit U2 comprises a single-chip microcomputer IC1, a capacitor C3, a resistor R6 and a capacitor C4.

Preferably, the CO sensor detection unit U3 comprises a sensor anti-polarization circuit, a sensor self-checking circuit, a primary amplifying circuit, a sensor J3, a primary filter, a secondary amplifying circuit, and a filter circuit.

Preferably, the alarm indication unit U4 comprises a lamp LED4, a lamp LED3, a resistor R27 and a resistor R28.

Preferably, the speed detection unit U5 comprises a normally-closed circuit comprising a MOS transistor Q2, a resistor R2, and a capacitor C2, a resistor R1, a resistor R3, a resistor R4, a diode D1, a transistor Q1, and a capacitor C10.

Preferably, the flameout control unit U6 comprises a switch tube Q1, a resistor R17, a resistor 18 and a capacitor C6.

In summary, when the generator generates excessive CO, the CO concentration in the environment is converted into a corresponding electrical signal by the CO sensor detection unit U3 to output to the MCU control unit U2 for processing. After processing by the MCU control unit U2, the signal is sent to the alarm indication unit and the flameout control unit, to give an alarm prompt of the CO concentration and shut down the generator, thereby preventing safety accidents.

DETAILED DESCRIPTION

Figure 1:
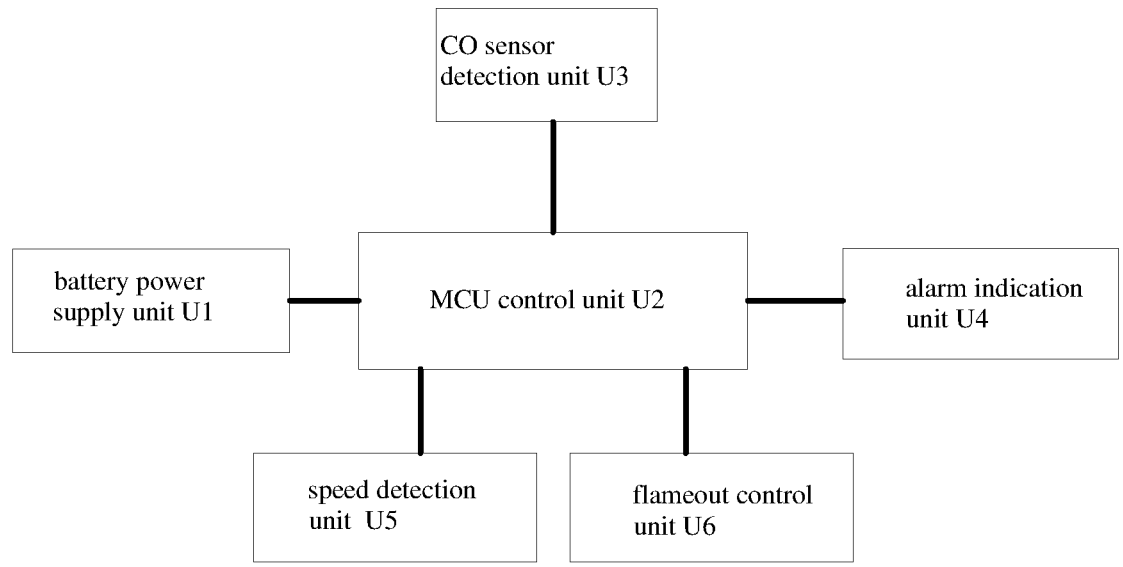
FIG. 1 is a structural representation of the present invention.
Figure 2:
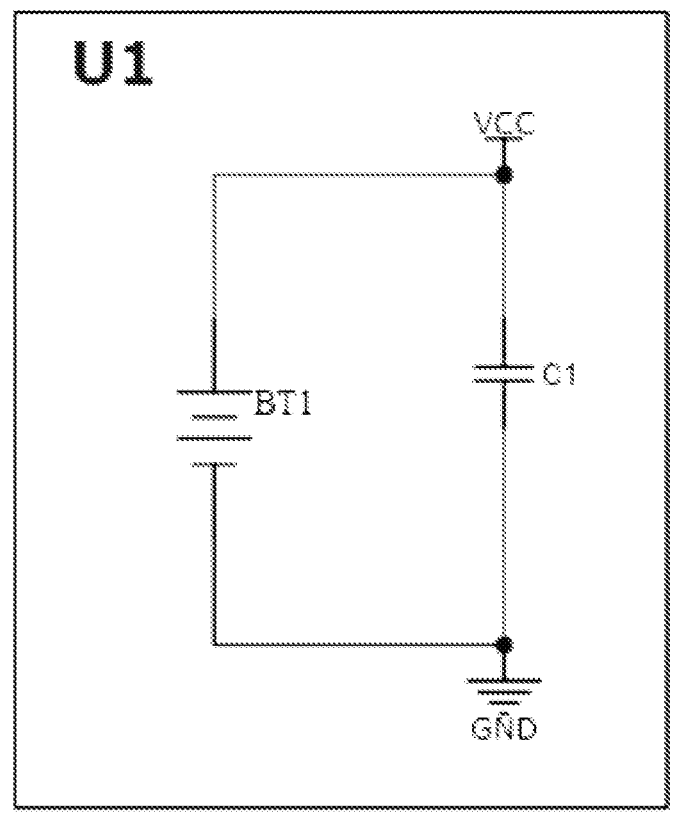
FIG. 2 is a circuit diagram of a battery power supply unit U1.
Figure 3:
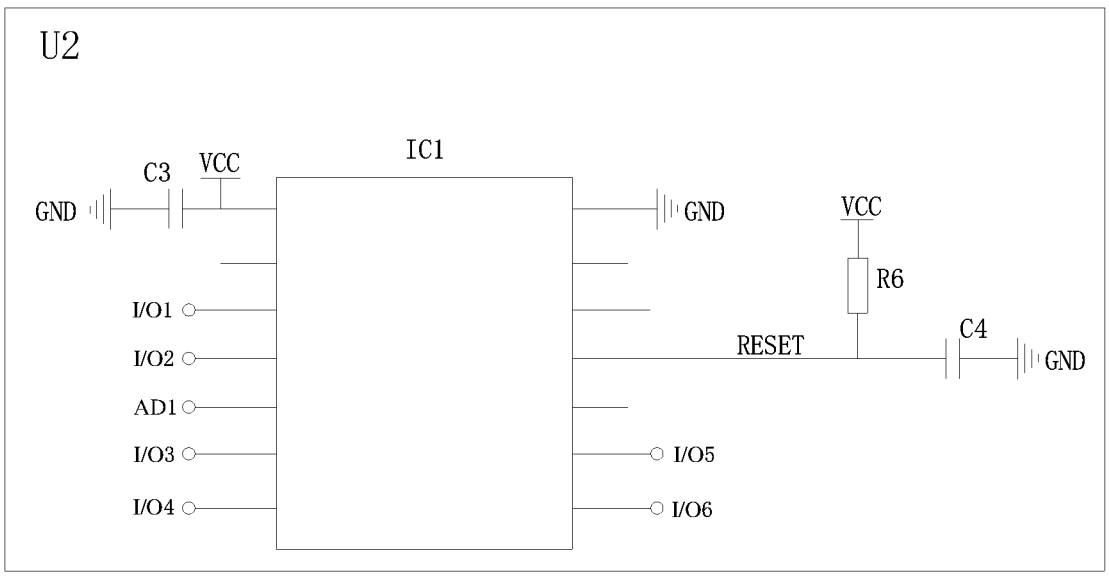
FIG. 3 is a circuit diagram of a MCU control unit U2.
Figure 4:
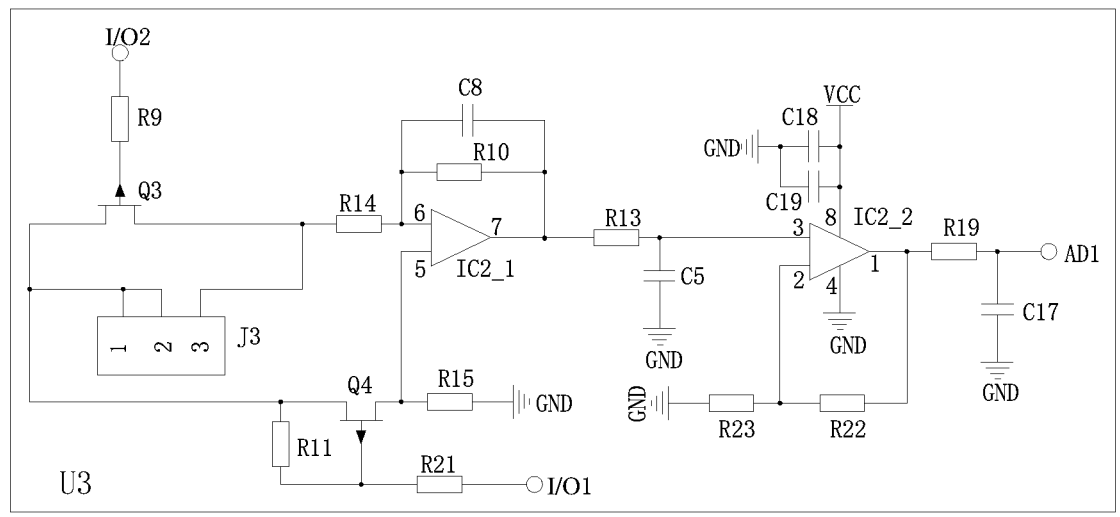
FIG. 4 is a circuit diagram of a CO sensor detection unit U3.
Figure 5:
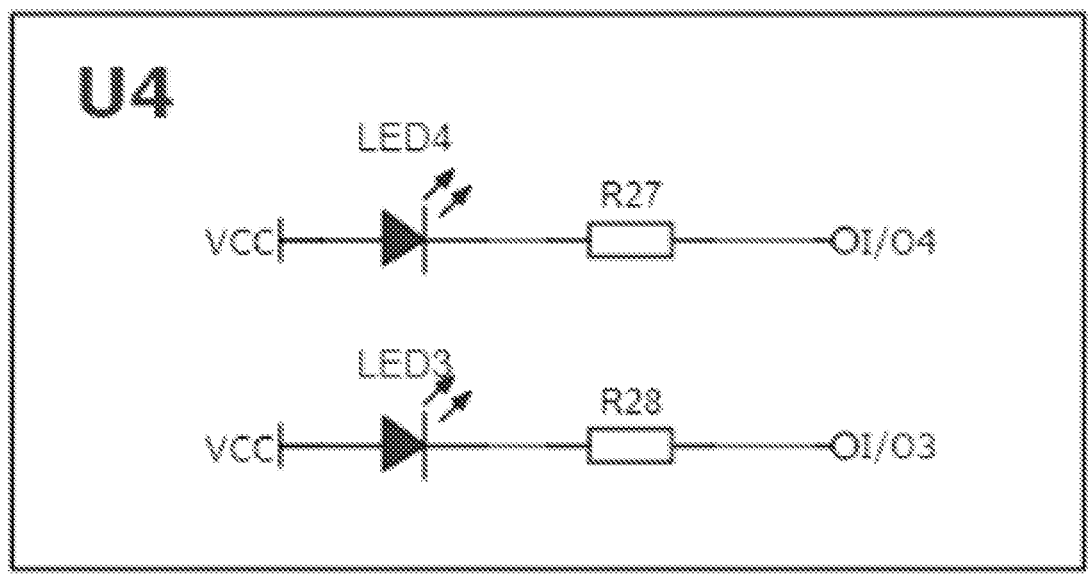
FIG. 5 is a circuit diagram of an alarm indication unit U4.
Figure 6:
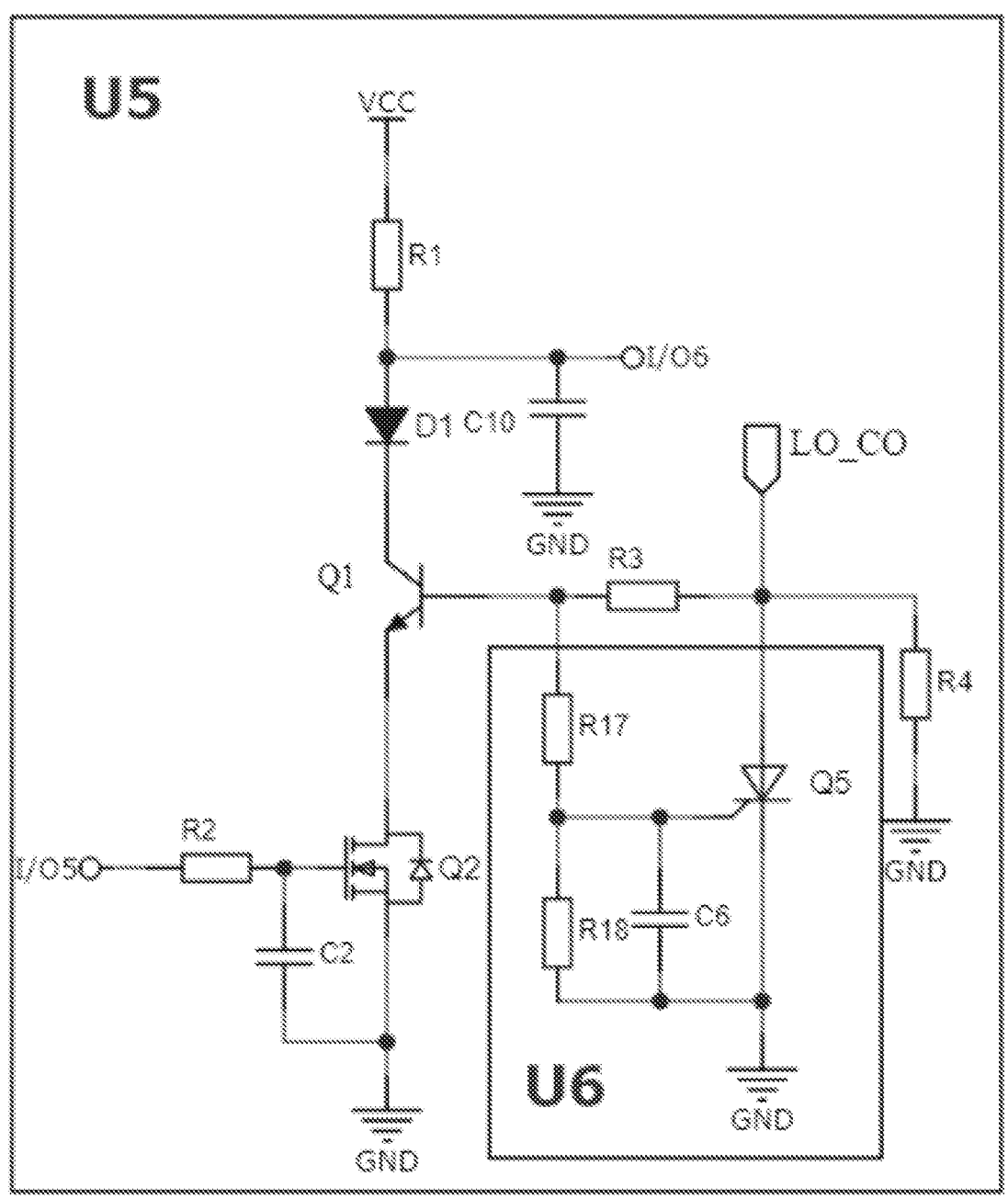
FIG. 6 is a circuit diagram of a speed detection unit U5.

As shown in FIGS. 1 to 6, a CO alarm for a battery type generator is provided, comprising a MCU control unit U2, a CO sensor detection unit U3, an alarm indication unit U4, a speed detection unit U5, a flameout control unit U6 and a battery power supply unit U1. Specifically, the MCU control unit U2 includes a single-chip microcomputer IC1, a capacitor C3, a resistor R6 and a capacitor C4. The single-chip microcomputer IC1 adopts a single-chip microcomputer with temperature detection, which can collect the ambient temperature of the MCU control unit U2 to compensate for changes in the gas sensor caused by temperature changes; the capacitor C4 is a filter capacitor, which filters a reset pin of the single-chip microcomputer IC1 through a resistor R4 and a capacitor C4; the capacitor C3 is a filter capacitor.

Specifically, the CO sensor detection unit U3 detects the concentration of CO gas and outputs a weak electrical signal, amplifies and outputs the weak electrical signal to the MCU control unit U2, and it includes a sensor anti-polarization circuit, a sensor self-checking circuit, a primary amplifying circuit, a sensor J3, a primary filter, a secondary amplifying circuit, and a filter circuit. The sensor anti-polarization circuit is composed of a resistor R9 and a switch tube Q3. The sensor self-checking circuit is composed of a resistor R11, a switch tube Q4, and a resistor R21. The primary amplifying circuit is composed of a resistor R14, a resistor R10, a capacitor C8, a resistor R15, and an operational amplifying unit IC2_1, and can amplify the electrical signal output by the sensor J3. The primary filter can be formed by a resistor R13 and a capacitor C5, and the capacitor C5 adopts a filter capacitor. The primary filter can filter the electrical signal amplified by the primary amplifying circuit and transmits it to the secondary amplifying circuit. The secondary amplifying circuit is composed of an operational amplifying unit IC2_2, capacitor C18, capacitor C19, a resistor R22 and a resistor R23, and can amplify the electrical signal from the primary filter. The filter circuit, formed by a resistor R19 and a capacitor C17, is configured to filter the electrical signal amplified by the second amplifying circuit, and transmits it to an AD1 port of the U2 module IC1.

Specifically, the alarm indication unit U4 includes a lamp LED4, a lamp LED3, a resistor R27, and a resistor R28. The lamp LED4 is a red lamp and is connected to the I/O4 pin of the single-chip microcomputer IC1 for CO concentration alarm indication. The CO concentration alarm indication includes CO concentration peak alarm indication and CO average concentration alarm indication; the lamp LED3 is a yellow lamp and is connected to the I/O3 pin of the single-chip microcomputer IC1 for module fault alarm indication. The fault alarm indications include battery low-voltage fault indication, alarm high-temperature fault indication, sensor fault indication, etc.; the resistor R27 and resistor R28 are current-limiting resistors.

Preferably, the speed detection unit U5 includes a normally-closed circuit, a resistor R1, a resistor R3, a resistor R4, a diode D1, a transistor Q1, a capacitor C10; the normally-closed circuit is composed of a MOS transistor Q2, a resistor R2, and a capacitor C2, and connects to an I/O5 pin of the single-chip microcomputer IC1; the resistor R1 is a pull-up resistor for the speed signal; the resistor R3 is a base current-limiting resistor of the transistor Q1; the resistor R4 is a pull-down bias resistor of the diode Q1 to prevent the diode Q1 from being triggered by mistake; the diode D1 prevents the input voltage from an externally connected engine igniter flameout module LO_CO from entering the module; the capacitor C10 is the filter capacitor, which filters the detected speed signal and inputs it to the I/O6 pin of the single-chip microcomputer ICE Specifically, the flameout control unit U6 includes switch tube Q5, a resistor R17, a resistor 18, and a capacitor C6; the resistor R17 and the switch tube Q5 control the ignition trigger voltage input by the externally connected engine igniter flameout module LO_CO, which is directly connected to the ground when flameout is necessary, to achieve the purpose of igniter flameout; the resistor R18 and the capacitor C6 form a filter circuit to prevent the switch tube Q5 from being triggered by mistake.

Specifically, the battery power supply unit includes a battery BT1 and a capacitor C1, and the battery BT1 is a non-rechargeable battery; the capacitor C1 is a filter capacitor that filters the battery output voltage.

What is claimed is:
1. A CO alarm for a battery type generator, comprising:
   a MCU control unit (U2), configured to analyze and process signals, which is in a deep sleep state when the generator is not running, and enters a sleep plus timing wake-up working state after the engine is running;
   a CO sensor detection unit (U3) connected to the MCU control unit, configured to convert the CO concentration in the environment into a corresponding electrical signal and output to the MCU control unit (U2) for processing, the CO sensor detection unit (U3) comprises a sensor anti-polarization circuit, a sensor self-checking circuit, a primary amplifying circuit, a primary filter, a sensor (J3), a secondary amplifying circuit and a filter circuit;
   an alarm indication unit (U4) connected to the MCU control unit, configured to give an alarm prompt for the CO concentration and an alarm failure prompt;
   a speed detection unit (U5) connected to the MCU control unit, configured to collect the running status of the generator and wake up the MCU control unit (U2) from the deep sleep state to the normal working state;
   a flameout control unit (U6) connected to the MCU control unit, configured to shut down the generator when the alarm fails or the CO concentration alarms;
   a battery power supply unit (U1), configured to provide a working power supply required for the entire CO alarm;
   wherein, the sensor anti-polarization circuit comprises a first resistor (R9) and a first switch tube (Q3); the sensor self-checking circuit comprises a second resistor (R11), a second switch tube (Q4) and a third resistor (R21);
   the primary amplifying circuit comprises a fourth resistor (R14), a fifth resistor (R10), a first capacitor (C8), a sixth resistor (R15), and a first operational amplifying unit (IC2_1), and is configured to amplify an electrical signal output by the sensor (J3);
   the primary filter comprises a seventh resistor (R13) and a second capacitor (C5), and is configured to filter and transmit the electrical signal amplified by the primary amplifying circuit to the secondary amplifying circuit;
   the secondary amplifying circuit comprises a second operational amplifying unit (IC2_2), a third capacitor (C18), a fourth capacitor (C19), an eighth resistor (R22) and a ninth resistor (R23), and is configured to amplify the electrical signal from the primary filter;
   the filter circuit comprises a tenth resistor (R19) and a fifth capacitor (C17), and is configured to filter and transmit the electrical signal amplified by the second amplifying circuit to the MCU control unit (U2).

2. The CO alarm for a battery type generator according to claim 1, wherein the battery power supply unit comprises a battery (BT1) and a sixth capacitor (C1).

3. The CO alarm for a battery type generator according to claim 1, wherein the MCU control unit (U2) comprises a single-chip microcomputer (IC1), a seventh capacitor (C3), an eleventh resistor (R6) and an eighth capacitor (C4).

4. The CO alarm for a battery type generator according to claim 1, wherein the alarm indication unit (U4) comprises a first lamp (LED4), a second lamp (LED3), a twelfth resistor (R27) and a thirteen resistor (R28).

5. The CO alarm for a battery type generator according to claim 1, wherein the speed detection unit (U5) comprises a normally-closed circuit comprising a MOS transistor (Q2), a fourteenth resistor (R2), and a ninth capacitor (C2), a fifteenth resistor (R1), a sixteenth resistor (R3), a seventeenth resistor (R4), a diode (D1), a transistor (Q1), and a tenth capacitor (C10).

6. The CO alarm for a battery type generator according to claim 1, wherein the flameout control unit (U6) comprises a third switch tube (Q5), an eighteenth resistor (R17), a nineteenth resistor (18) and an eleventh capacitor (C6).

\* \* \* \* \*